United States Patent [19]

Rothe et al.

[11] Patent Number: 5,854,003
[45] Date of Patent: Dec. 29, 1998

[54] SCREENING METHOD FOR AGENTS THAT MODULATE HUMAN NIK ACTIVITY

[75] Inventors: Mike Rothe, San Mateo; Lin Wu, South San Francisco, both of Calif.

[73] Assignee: Tularik Inc., South San Francisco, Calif.

[21] Appl. No.: 32,475

[22] Filed: Feb. 26, 1998

Related U.S. Application Data

[62] Division of Ser. No. 887,518, Jul. 3, 1997.

[51] Int. Cl.$^6$ .................................................. G01N 33/566
[52] U.S. Cl. .............................................................. 435/7.8
[58] Field of Search .............................. 435/7.8; 530/324, 530/325, 326, 327, 328, 350

[56] References Cited

PUBLICATIONS

Malinin et al, Nature, vol. 385, pp. 540–544, Feb. 6, 1997.

*Primary Examiner*—Terry A. McKelvey
*Attorney, Agent, or Firm*—Richard Aron Osman

[57] ABSTRACT

The invention provides methods and compositions relating to a novel kinase, NIK, involved in NFκB activation. The polypeptides may be produced recombinantly from transformed host cells from the disclosed NIK encoding nucleic acids or purified from human cells. The invention provides isolated NIK hybridization probes and primers capable of specifically hybridizing with the disclosed NIK genes, NIK-specific binding agents such as specific antibodies, and methods of making and using the subject compositions in diagnosis, therapy and in the biopharmaceutical industry.

9 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
       ( A ) LENGTH: 3156 base pairs
       ( B ) TYPE: nucleic acid
       ( C ) STRANDEDNESS: double
       ( D ) TOPOLOGY: linear ( i i ) MOLECULE TYPE: cDNA ( x i ) SEQUENCE DESCRIPTION: SEQ ID NO:1:

```
ATGGCAGTGA  TGGAAATGGC  CTGCCCAGGT  GCCCCTGGCT  CAGCAGTGGG  GCAGCAGAAG    60
GAACTCCCCA  AAGCCAAGGA  GAAGACGCCG  CCACTGGGGA  AGAAACAGAG  CTCCGTCTAC   120
AAGCTTGAGG  CCGTGGAGAA  GAGCCCTGTG  TTCTGCGGAA  AGTGGGAGAT  CCTGAATGAC   180
GTGATTACCA  AGGGCACAGC  CAAGGAAGGC  TCCGAGGCAG  GGCCAGCTGC  CATCTCTATC   240
ATCGCCCAGG  CTGAGTGTGA  GAATAGCCAA  GAGTTCAGCC  CCACCTTTTC  AGAACGCATT   300
TTCATCGCTG  GGTCCAAACA  GTACAGCCAG  TCCGAGAGTC  TTGATCAGAT  CCCCAACAAT   360
GTGGCCCATG  CTACAGAGGG  CAAAATGGCC  CGTGTGTGTT  GGAAGGGAAA  GCGTCGCAGC   420
AAAGCCCGGA  AGAAACGGAA  GAAGAAGAGC  TCAAAGTCCC  TGGCTCATGC  AGGAGTGGCC   480
TTGGCCAAAC  CCCTCCCCAG  GACCCCTGAG  CAGGAGAGCT  GCACCATCCC  AGTGCAGGAG   540
GATGAGTCTC  CACTCGGCGC  CCCATATGTT  AGAAACACCC  CGCAGTTCAC  CAAGCCTCTG   600
AAGGAACCAG  GCCTTGGGCA  ACTCTGTTTT  AAGCAGCTTG  GCGAGGGCCT  ACGGCCGGCT   660
CTGCCTCGAT  CAGAACTCCA  CAAACTGATC  AGCCCCTTGC  AATGTCTGAA  CCACGTGTGG   720
AAACTGCACC  ACCCCCAGGA  CGGAGGCCCC  CTGCCCCTGC  CCACGCACCC  CTTCCCCTAT   780
AGCAGACTGC  CTCATCCCTT  CCCATTCCAC  CCTCTCCAGC  CCTGGAAACC  TCACCCTCTG   840
GAGTCCTTCC  TGGGCAAACT  GGCCTGTGTA  GACAGCCAGA  AACCCTTGCC  TGACCCACAC   900
CTGAGCAAAC  TGGCCTGTGT  AGACAGTCCA  AAGCCCTGC   CTGGCCACA   CCTGGAGCCC   960
AGCTGCCTGT  CTCGTGGTGC  CCATGAGAAG  TTTTCTGTGG  AGGAATACCT  AGTGCATGCT  1020
CTGCAAGGCA  GCGTGAGCTC  AAGCCAGGCC  CACAGCCTGA  CCAGCCTGGC  CAAGACCTGG  1080
GCAGCACGGG  GCTCCAGATC  CCGGGAGCCC  AGCCCAAAA   CTGAGGACAA  CGAGGGTGTC  1140
CTGCTCACTG  AGAAACTCAA  GCCAGTGGAT  TATGAGTACC  GAGAAGAAGT  CCACTGGGCC  1200
ACGCACCAGC  TCCGCCTGGG  CAGAGGCTCC  TTCGGAGAGG  TGCACAGGAT  GGAGGACAAG  1260
CAGACTGGCT  TCCAGTGCGC  TGTCAAAAAG  GTGCGGCTGG  AAGTATTTCG  GGCAGAGGAG  1320
```

```
CTGATGGCAT  GTGCAGGATT  GACCTCACCC  AGAATTGTCC  CTTTGTATGG  AGCTGTGAGA   1380
GAAGGGCCTT  GGGTCAACAT  CTTCATGGAG  CTGCTGGAAG  GTGGCTCCCT  GGGCCAGCTG   1440
GTCAAGGAGC  AGGGCTGTCT  CCCAGAGGAC  CGGGCCCTGT  ACTACCTGGG  CCAGGCCCTG   1500
GAGGGTCTGG  AATACCTCCA  CTCACGAAGG  ATTCTGCATG  GGGACGTCAA  AGCTGACAAC   1560
GTGCTCCTGT  CCAGCGATGG  GAGCCACGCA  GCCCTCTGTG  ACTTTGGCCA  TGCTGTGTGT   1620
CTTCAACCTG  ATGGCCTGGG  AAAGTCCTTG  CTCACAGGGG  ACTACATCCC  TGGCACAGAG   1680
ACCCACATGG  CTCCGGAGGT  GGTGCTGGGC  AGGAGCTGCG  ACGCCAAGGT  GGATGTCTGG   1740
AGCAGCTGCT  GTATGATGCT  GCACATGCTC  AACGGCTGCC  ACCCCTGGAC  TCAGTTCTTC   1800
CGAGGGCCGC  TCTGCCTCAA  GATTGCCAGC  GAGCCTCCGC  CTGTGAGGGA  GATCCACCC    1860
TCCTGCGCCC  CTCTCACAGC  CCAGGCCATC  AAGAGGGGC   TGAGGAAAGA  GCCCATCCAC   1920
CGCGTGTCTG  CAGCGGAGCT  GGGAGGGAAG  GTGAACCGGG  CACTACAGCA  AGTGGGAGGT   1980
CTGAAGAGCC  CTTGGAGGGG  AGAATATAAA  GAACCAAGAC  ATCCACCGCC  AAATCAAGCC   2040
AATTACCACC  AGACCCTCCA  TGCCCAGCCG  AGAGAGCTTT  CGCCAAGGGC  CCCAGGGCCC   2100
CGGCCAGCTG  AGGAGACAAC  AGGCAGAGCC  CCTAAGCTCC  AGCCTCCTCT  CCCACCAGAG   2160
CCCCCAGAGC  CAAACAAGTC  TCCTCCCTTG  ACTTTGAGCA  AGGAGGAGTC  TGGGATGTGG   2220
GAACCCTTAC  CTCTGTCCTC  CCTGGAGCCA  GCCCTGCCA   GAAACCCCAG  CTCACCAGAG   2280
CGGAAAGCAA  CCGTCCCGGA  GCAGGAACTG  CAGCAGCTGG  AAATAGAATT  ATTCCTCAAC   2340
AGCCTGTCCC  AGCCATTTTC  TCTGGAGGAG  CAGGAGCAAA  TTCTCTCGTG  CCTCAGCATC   2400
GACAGCCTCT  CCCTGTCGGA  TGACAGTGAG  AAGAACCCAT  CAAAGGCCTC  TCAAAGCTCG   2460
CGGGACACCC  TGAGCTCAGG  CGTACACTCC  TGGAGCAGCC  AGGCCGAGGC  TCGAAGCTCC   2520
AGCTGGAACA  TGGTGCTGGC  CCGGGGGCGG  CCCACCGACA  CCCCAAGCTA  TTTCAATGGT   2580
GTGAAAGTCC  AAATACAGTC  TCTTAATGGT  GAACACCTGC  ACATCCGGGA  GTTCCACCGG   2640
GTCAAAGTGG  GAGACATCGC  CACTGGCATC  AGCAGCCAGA  TCCCAGCTGC  AGCCTTCAGC   2700
TTGGTCACCA  AAGACGGGCA  GCCTGTTCGC  TACGACATGG  AGGTGCCAGA  CTCGGGCATC   2760
GACCTGCAGT  GCACACTGGC  CCCTGATGGC  AGCTTCGCCT  GGAGCTGGAG  GGTCAAGCAT   2820
GGCCAGCTGG  AGAACAGGCC  CTAACCCTGC  CCTCCACCGC  CGGCTCCACA  CTGCCGGAAA   2880
GCAGCCTTCC  TGCTCGGTGC  ACGATGCTGC  CCTGAAAACA  CAGGCTCAGC  CGTTCCCAGG   2940
GGATTGCCAG  CCCCCCGGCT  CACAGTGGGA  ACCAGGGCCT  CGCAGCAGCA  AGGTGGGGC    3000
AAGCAGAATG  CCTCCCAGGA  TTTCACACCT  GAGCCCTGCC  CCACCCTGCT  GAAAAAACAT   3060
CCGCCACGTG  AAGAGACAGA  AGGAGGATGG  CAGGAGTTAC  CTGGGGAAAC  AAAACAGGGA   3120
TCTTTTTCTG  CCCCTGCTCC  AGTCGAGTTG  GCCTGA                              3156
```

( 2 ) INFORMATION FOR SEQ ID NO:2:

( i ) SEQUENCE CHARACTERISTICS:
        ( A ) LENGTH: 947 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met  Ala  Val  Met  Glu  Met  Ala  Cys  Pro  Gly  Ala  Pro  Gly  Ser  Ala  Val
 1              5                        10                       15
```

-continued

```
Gly Gln Gln Lys Glu Leu Pro Lys Ala Lys Glu Lys Thr Pro Pro Leu
             20                  25                  30
Gly Lys Lys Gln Ser Ser Val Tyr Lys Leu Glu Ala Val Glu Lys Ser
             35                  40                  45
Pro Val Phe Cys Gly Lys Trp Glu Ile Leu Asn Asp Val Ile Thr Lys
     50                  55                  60
Gly Thr Ala Lys Glu Gly Ser Glu Ala Gly Pro Ala Ala Ile Ser Ile
 65                  70                  75                  80
Ile Ala Gln Ala Glu Cys Glu Asn Ser Gln Glu Phe Ser Pro Thr Phe
                 85                  90                  95
Ser Glu Arg Ile Phe Ile Ala Gly Ser Lys Gln Tyr Ser Gln Ser Glu
             100                 105                 110
Ser Leu Asp Gln Ile Pro Asn Asn Val Ala His Ala Thr Glu Gly Lys
         115                 120                 125
Met Ala Arg Val Cys Trp Lys Gly Lys Arg Arg Ser Lys Ala Arg Lys
     130                 135                 140
Lys Arg Lys Lys Lys Ser Ser Lys Ser Leu Ala His Ala Gly Val Ala
145                 150                 155                 160
Leu Ala Lys Pro Leu Pro Arg Thr Pro Glu Gln Glu Ser Cys Thr Ile
                 165                 170                 175
Pro Val Gln Glu Asp Glu Ser Pro Leu Gly Ala Pro Tyr Val Arg Asn
             180                 185                 190
Thr Pro Gln Phe Thr Lys Pro Leu Lys Glu Pro Gly Leu Gly Gln Leu
         195                 200                 205
Cys Phe Lys Gln Leu Gly Glu Gly Leu Arg Pro Ala Leu Pro Arg Ser
     210                 215                 220
Glu Leu His Lys Leu Ile Ser Pro Leu Gln Cys Leu Asn His Val Trp
225                 230                 235                 240
Lys Leu His His Pro Gln Asp Gly Gly Pro Leu Pro Leu Pro Thr His
                 245                 250                 255
Pro Phe Pro Tyr Ser Arg Leu Pro His Pro Phe Pro Phe His Pro Leu
             260                 265                 270
Gln Pro Trp Lys Pro His Pro Leu Glu Ser Phe Leu Gly Lys Leu Ala
         275                 280                 285
Cys Val Asp Ser Gln Lys Pro Leu Pro Asp Pro His Leu Ser Lys Leu
     290                 295                 300
Ala Cys Val Asp Ser Pro Lys Pro Leu Pro Gly Pro His Leu Glu Pro
305                 310                 315                 320
Ser Cys Leu Ser Arg Gly Ala His Glu Lys Phe Ser Val Glu Glu Tyr
                 325                 330                 335
Leu Val His Ala Leu Gln Gly Ser Val Ser Ser Ser Gln Ala His Ser
             340                 345                 350
Leu Thr Ser Leu Ala Lys Thr Trp Ala Ala Arg Gly Ser Arg Ser Arg
         355                 360                 365
Glu Pro Ser Pro Lys Thr Glu Asp Asn Glu Gly Val Leu Leu Thr Glu
     370                 375                 380
Lys Leu Lys Pro Val Asp Tyr Glu Tyr Arg Glu Glu Val His Trp Ala
385                 390                 395                 400
Thr His Gln Leu Arg Leu Gly Arg Gly Ser Phe Gly Glu Val His Arg
                 405                 410                 415
Met Glu Asp Lys Gln Thr Gly Phe Gln Cys Ala Val Lys Lys Val Arg
             420                 425                 430
Leu Glu Val Phe Arg Ala Glu Glu Leu Met Ala Cys Ala Gly Leu Thr
         435                 440                 445
```

```
Ser  Pro  Arg  Ile  Val  Pro  Leu  Tyr  Gly  Ala  Val  Arg  Glu  Gly  Pro  Trp
450                      455                      460

Val  Asn  Ile  Phe  Met  Glu  Leu  Leu  Glu  Gly  Gly  Ser  Leu  Gly  Gln  Leu
465                      470                      475                      480

Val  Lys  Glu  Gln  Gly  Cys  Leu  Pro  Glu  Asp  Arg  Ala  Leu  Tyr  Tyr  Leu
                    485                      490                      495

Gly  Gln  Ala  Leu  Glu  Gly  Leu  Glu  Tyr  Leu  His  Ser  Arg  Arg  Ile  Leu
               500                      505                      510

His  Gly  Asp  Val  Lys  Ala  Asp  Asn  Val  Leu  Leu  Ser  Ser  Asp  Gly  Ser
          515                      520                      525

His  Ala  Ala  Leu  Cys  Asp  Phe  Gly  His  Ala  Val  Cys  Leu  Gln  Pro  Asp
530                      535                      540

Gly  Leu  Gly  Lys  Ser  Leu  Leu  Thr  Gly  Asp  Tyr  Ile  Pro  Gly  Thr  Glu
545                      550                      555                      560

Thr  His  Met  Ala  Pro  Glu  Val  Val  Leu  Gly  Arg  Ser  Cys  Asp  Ala  Lys
                    565                      570                      575

Val  Asp  Val  Trp  Ser  Ser  Cys  Cys  Met  Met  Leu  His  Met  Leu  Asn  Gly
               580                      585                      590

Cys  His  Pro  Trp  Thr  Gln  Phe  Phe  Arg  Gly  Pro  Leu  Cys  Leu  Lys  Ile
          595                      600                      605

Ala  Ser  Glu  Pro  Pro  Pro  Val  Arg  Glu  Ile  Pro  Pro  Ser  Cys  Ala  Pro
610                      615                      620

Leu  Thr  Ala  Gln  Ala  Ile  Gln  Glu  Gly  Leu  Arg  Lys  Glu  Pro  Ile  His
625                      630                      635                      640

Arg  Val  Ser  Ala  Ala  Glu  Leu  Gly  Gly  Lys  Val  Asn  Arg  Ala  Leu  Gln
                    645                      650                      655

Gln  Val  Gly  Gly  Leu  Lys  Ser  Pro  Trp  Arg  Gly  Glu  Tyr  Lys  Glu  Pro
               660                      665                      670

Arg  His  Pro  Pro  Pro  Asn  Gln  Ala  Asn  Tyr  His  Gln  Thr  Leu  His  Ala
          675                      680                      685

Gln  Pro  Arg  Glu  Leu  Ser  Pro  Arg  Ala  Pro  Gly  Pro  Arg  Pro  Ala  Glu
     690                      695                      700

Glu  Thr  Thr  Gly  Arg  Ala  Pro  Lys  Leu  Gln  Pro  Pro  Leu  Pro  Pro  Glu
705                      710                      715                      720

Pro  Pro  Glu  Pro  Asn  Lys  Ser  Pro  Pro  Leu  Thr  Leu  Ser  Lys  Glu  Glu
               725                      730                      735

Ser  Gly  Met  Trp  Glu  Pro  Leu  Pro  Leu  Ser  Ser  Leu  Glu  Pro  Ala  Pro
               740                      745                      750

Ala  Arg  Asn  Pro  Ser  Ser  Pro  Glu  Arg  Lys  Ala  Thr  Val  Pro  Glu  Gln
          755                      760                      765

Glu  Leu  Gln  Gln  Leu  Glu  Ile  Glu  Leu  Phe  Leu  Asn  Ser  Leu  Ser  Gln
     770                      775                      780

Pro  Phe  Ser  Leu  Glu  Glu  Gln  Glu  Gln  Ile  Leu  Ser  Cys  Leu  Ser  Ile
785                      790                      795                      800

Asp  Ser  Leu  Ser  Leu  Ser  Asp  Asp  Ser  Glu  Lys  Asn  Pro  Ser  Lys  Ala
                    805                      810                      815

Ser  Gln  Ser  Ser  Arg  Asp  Thr  Leu  Ser  Ser  Gly  Val  His  Ser  Trp  Ser
               820                      825                      830

Ser  Gln  Ala  Glu  Ala  Arg  Ser  Ser  Trp  Asn  Met  Val  Leu  Ala  Arg
          835                      840                      845

Gly  Arg  Pro  Thr  Asp  Thr  Pro  Ser  Tyr  Phe  Asn  Gly  Val  Lys  Val  Gln
850                      855                      860
```

| Ile | Gln | Ser | Leu | Asn | Gly | Glu | His | Leu | His | Ile | Arg | Glu | Phe | His | Arg |
|---|---|---|---|---|---|---|---|---|---|---|---|---|---|---|---|
| 865 | | | | | 870 | | | | | 875 | | | | | 880 |

| Val | Lys | Val | Gly | Asp | Ile | Ala | Thr | Gly | Ile | Ser | Ser | Gln | Ile | Pro | Ala |
|---|---|---|---|---|---|---|---|---|---|---|---|---|---|---|---|
| | | | | 885 | | | | 890 | | | | | | 895 | |

| Ala | Ala | Phe | Ser | Leu | Val | Thr | Lys | Asp | Gly | Gln | Pro | Val | Arg | Tyr | Asp |
|---|---|---|---|---|---|---|---|---|---|---|---|---|---|---|---|
| | | | 900 | | | | | 905 | | | | | 910 | | |

| Met | Glu | Val | Pro | Asp | Ser | Gly | Ile | Asp | Leu | Gln | Cys | Thr | Leu | Ala | Pro |
|---|---|---|---|---|---|---|---|---|---|---|---|---|---|---|---|
| | | 915 | | | | | 920 | | | | | 925 | | | |

| Asp | Gly | Ser | Phe | Ala | Trp | Ser | Trp | Arg | Val | Lys | His | Gly | Gln | Leu | Glu |
|---|---|---|---|---|---|---|---|---|---|---|---|---|---|---|---|
| | 930 | | | | | 935 | | | | | 940 | | | | |

| Asn | Arg | Pro |
|---|---|---|
| 945 | | |

(2) INFORMATION FOR SEQ ID NO:3:

(i) SEQUENCE CHARACTERISTICS:
        (A) LENGTH: 745 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

| Met | Glu | Arg | Pro | Pro | Gly | Leu | Arg | Pro | Gly | Ala | Gly | Gly | Pro | Trp | Glu |
|---|---|---|---|---|---|---|---|---|---|---|---|---|---|---|---|
| 1 | | | | 5 | | | | | 10 | | | | | 15 | |

| Met | Arg | Glu | Arg | Leu | Gly | Thr | Gly | Gly | Phe | Gly | Asn | Val | Cys | Leu | Tyr |
|---|---|---|---|---|---|---|---|---|---|---|---|---|---|---|---|
| | | | 20 | | | | | 25 | | | | | 30 | | |

| Gln | His | Arg | Glu | Leu | Asp | Leu | Lys | Ile | Ala | Ile | Lys | Ser | Cys | Arg | Leu |
|---|---|---|---|---|---|---|---|---|---|---|---|---|---|---|---|
| | | 35 | | | | | 40 | | | | | 45 | | | |

| Glu | Leu | Ser | Thr | Lys | Asn | Arg | Glu | Arg | Trp | Cys | His | Glu | Ile | Gln | Ile |
|---|---|---|---|---|---|---|---|---|---|---|---|---|---|---|---|
| | 50 | | | | | 55 | | | | | 60 | | | | |

| Met | Lys | Lys | Leu | Asn | His | Ala | Asn | Val | Val | Lys | Ala | Cys | Asp | Val | Pro |
|---|---|---|---|---|---|---|---|---|---|---|---|---|---|---|---|
| 65 | | | | | 70 | | | | | 75 | | | | | 80 |

| Glu | Glu | Leu | Asn | Ile | Leu | Ile | His | Asp | Val | Pro | Leu | Leu | Ala | Met | Glu |
|---|---|---|---|---|---|---|---|---|---|---|---|---|---|---|---|
| | | | | 85 | | | | | 90 | | | | | | 95 |

| Tyr | Cys | Ser | Gly | Gly | Asp | Leu | Arg | Lys | Leu | Leu | Asn | Lys | Pro | Glu | Asn |
|---|---|---|---|---|---|---|---|---|---|---|---|---|---|---|---|
| | | | | 100 | | | | 105 | | | | | 110 | | |

| Cys | Cys | Gly | Leu | Lys | Glu | Ser | Gln | Ile | Leu | Ser | Leu | Leu | Ser | Asp | Ile |
|---|---|---|---|---|---|---|---|---|---|---|---|---|---|---|---|
| | | | 115 | | | | | 120 | | | | | 125 | | |

| Gly | Ser | Gly | Ile | Arg | Tyr | Leu | His | Glu | Asn | Lys | Ile | Ile | His | Arg | Asp |
|---|---|---|---|---|---|---|---|---|---|---|---|---|---|---|---|
| | | 130 | | | | | 135 | | | | | 140 | | | |

| Leu | Lys | Pro | Glu | Asn | Ile | Val | Leu | Gln | Asp | Val | Gly | Gly | Lys | Ile | Ile |
|---|---|---|---|---|---|---|---|---|---|---|---|---|---|---|---|
| 145 | | | | | 150 | | | | | 155 | | | | | 160 |

| His | Lys | Ile | Ile | Asp | Leu | Gly | Tyr | Ala | Lys | Asp | Val | Asp | Gln | Gly | Ser |
|---|---|---|---|---|---|---|---|---|---|---|---|---|---|---|---|
| | | | | 165 | | | | | 170 | | | | | 175 | |

| Leu | Cys | Thr | Ser | Phe | Val | Gly | Thr | Leu | Gln | Tyr | Leu | Ala | Pro | Glu | Leu |
|---|---|---|---|---|---|---|---|---|---|---|---|---|---|---|---|
| | | | 180 | | | | | 185 | | | | | 190 | | |

| Phe | Glu | Asn | Lys | Pro | Tyr | Thr | Ala | Thr | Val | Asp | Tyr | Trp | Ser | Phe | Gly |
|---|---|---|---|---|---|---|---|---|---|---|---|---|---|---|---|
| | | | 195 | | | | | 200 | | | | | 205 | | |

| Thr | Met | Val | Phe | Glu | Cys | Ile | Ala | Gly | Tyr | Arg | Pro | Phe | Leu | His | His |
|---|---|---|---|---|---|---|---|---|---|---|---|---|---|---|---|
| | | 210 | | | | | 215 | | | | | 220 | | | |

| Leu | Gln | Pro | Phe | Thr | Trp | His | Glu | Lys | Ile | Lys | Lys | Lys | Asp | Pro | Lys |
|---|---|---|---|---|---|---|---|---|---|---|---|---|---|---|---|
| 225 | | | | | 230 | | | | | 235 | | | | | 240 |

| Cys | Ile | Phe | Ala | Cys | Glu | Glu | Met | Ser | Gly | Glu | Val | Arg | Phe | Ser | Ser |
|---|---|---|---|---|---|---|---|---|---|---|---|---|---|---|---|
| | | | | 245 | | | | | 250 | | | | | 255 | |

```
His Leu Pro Gln Pro Asn Ser Leu Cys Ser Leu Ile Val Glu Pro Met
            260                 265                 270
Glu Asn Trp Leu Gln Leu Met Leu Asn Trp Asp Pro Gln Arg Gly
        275                 280                 285
Gly Pro Val Asp Leu Thr Leu Lys Gln Pro Arg Cys Phe Val Leu Met
    290                 295                 300
Asp His Ile Leu Asn Leu Lys Ile Val His Ile Leu Asn Met Thr Ser
305                     310                 315                 320
Ala Lys Ile Ile Ser Phe Leu Leu Pro Pro Asp Glu Ser Leu His Ser
                325                 330                 335
Leu Gln Ser Arg Ile Glu Arg Glu Thr Gly Ile Asn Thr Gly Ser Gln
            340                 345                 350
Glu Leu Leu Ser Glu Thr Gly Ile Ser Leu Asp Pro Arg Lys Pro Ala
        355                 360                 365
Ser Gln Cys Val Leu Asp Gly Val Arg Gly Cys Asp Ser Tyr Met Val
    370                 375                 380
Tyr Leu Phe Asp Lys Ser Lys Thr Val Tyr Glu Gly Pro Phe Ala Ser
385                 390                 395                 400
Arg Ser Leu Ser Asp Cys Val Asn Tyr Ile Val Gln Asp Ser Lys Ile
                405                 410                 415
Gln Leu Pro Ile Ile Gln Leu Arg Lys Val Trp Ala Glu Ala Val His
            420                 425                 430
Tyr Val Ser Gly Leu Lys Glu Asp Tyr Ser Arg Leu Phe Gln Gly Gln
        435                 440                 445
Arg Ala Ala Met Leu Ser Leu Leu Arg Tyr Asn Ala Asn Leu Thr Lys
    450                 455                 460
Met Lys Asn Thr Leu Ile Ser Ala Ser Gln Gln Leu Lys Ala Lys Leu
465                     470                 475                 480
Glu Phe Phe His Lys Ser Ile Gln Leu Asp Leu Glu Arg Tyr Ser Glu
                485                 490                 495
Gln Met Thr Tyr Gly Ile Ser Ser Glu Lys Met Leu Lys Ala Trp Lys
            500                 505                 510
Glu Met Glu Glu Lys Ala Ile His Tyr Ala Glu Val Gly Val Ile Gly
        515                 520                 525
Tyr Leu Glu Asp Gln Ile Met Ser Leu His Ala Glu Ile Met Glu Leu
    530                 535                 540
Gln Lys Ser Pro Tyr Gly Arg Arg Gln Gly Asp Leu Met Glu Ser Leu
545                 550                 555                 560
Glu Gln Arg Ala Ile Asp Leu Tyr Lys Gln Leu Lys His Arg Pro Ser
                565                 570                 575
Asp His Ser Tyr Ser Asp Ser Thr Glu Met Val Lys Ile Ile Val His
            580                 585                 590
Thr Val Gln Ser Gln Asp Arg Val Leu Lys Glu Arg Phe Gly His Leu
        595                 600                 605
Ser Lys Leu Leu Gly Cys Lys Gln Lys Ile Ile Asp Leu Leu Pro Lys
    610                 615                 620
Val Glu Val Ala Leu Ser Asn Ile Lys Glu Ala Asp Asn Thr Val Met
625                 630                 635                 640
Phe Met Gln Gly Lys Arg Gln Lys Glu Ile Trp His Leu Leu Lys Ile
                645                 650                 655
Ala Cys Thr Gln Ser Ser Ala Arg Ser Leu Val Gly Ser Ser Leu Glu
            660                 665                 670
Gly Ala Val Thr Pro Gln Ala Tyr Ala Trp Leu Ala Pro Asp Leu Ala
        675                 680                 685
```

-continued

```
Glu  His  Asp  His  Ser  Leu  Ser  Cys  Val  Val  Thr  Pro  Gln  Asp  Gly  Glu
     690                 695                 700

Thr  Ser  Ala  Gln  Met  Ile  Glu  Glu  Asn  Leu  Asn  Cys  Leu  Gly  His  Leu
705                      710                 715                           720

Ser  Thr  Ile  Ile  His  Glu  Ala  Asn  Glu  Gln  Gly  Asn  Ser  Met  Met
                    725                 730                      735

Asn  Leu  Asp  Trp  Ser  Trp  Leu  Thr  Glu
               740                      745
```

( 2 ) INFORMATION FOR SEQ ID NO:4:

( i ) SEQUENCE CHARACTERISTICS:
        ( A ) LENGTH: 756 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met  Ser  Trp  Ser  Pro  Ser  Leu  Thr  Thr  Gln  Thr  Cys  Gly  Ala  Trp  Glu
1                   5                   10                      15

Met  Lys  Glu  Arg  Leu  Gly  Thr  Gly  Gly  Phe  Gly  Asn  Val  Ile  Arg  Trp
               20                  25                      30

His  Asn  Gln  Glu  Thr  Gly  Glu  Gln  Ile  Ala  Ile  Lys  Gln  Cys  Arg  Gln
               35                  40                      45

Glu  Leu  Ser  Pro  Arg  Asn  Arg  Glu  Arg  Trp  Cys  Leu  Glu  Ile  Gln  Ile
     50                  55                       60

Met  Arg  Arg  Leu  Thr  His  Pro  Asn  Val  Val  Ala  Ala  Arg  Asp  Val  Pro
65                       70                  75                            80

Glu  Gly  Met  Gln  Asn  Leu  Ala  Pro  Asn  Asp  Leu  Pro  Leu  Leu  Ala  Met
               85                       90                       95

Glu  Tyr  Cys  Gln  Gly  Gly  Asp  Leu  Arg  Lys  Tyr  Leu  Asn  Gln  Phe  Glu
               100                 105                      110

Asn  Cys  Cys  Gly  Leu  Arg  Glu  Gly  Ala  Ile  Leu  Thr  Leu  Leu  Ser  Asp
          115                 120                 125

Ile  Ala  Ser  Ala  Leu  Arg  Tyr  Leu  His  Glu  Asn  Arg  Ile  Ile  His  Arg
     130                 135                 140

Asp  Leu  Lys  Pro  Glu  Asn  Ile  Val  Leu  Gln  Gln  Gly  Glu  Gln  Arg  Leu
145                      150                 155                           160

Ile  His  Lys  Ile  Ile  Asp  Leu  Gly  Tyr  Ala  Lys  Glu  Leu  Asp  Gln  Gly
               165                 170                      175

Ser  Leu  Cys  Thr  Ser  Phe  Val  Gly  Thr  Leu  Gln  Tyr  Leu  Ala  Pro  Glu
          180                 185                 190

Leu  Leu  Glu  Gln  Gln  Lys  Tyr  Thr  Val  Thr  Val  Asp  Tyr  Trp  Ser  Phe
          195                 200                 205

Gly  Thr  Leu  Ala  Phe  Glu  Cys  Ile  Thr  Gly  Phe  Arg  Pro  Phe  Leu  Pro
     210                 215                 220

Asn  Trp  Gln  Pro  Val  Gln  Trp  His  Ser  Lys  Val  Arg  Gln  Lys  Ser  Glu
225                      230                 235                           240

Val  Asp  Ile  Val  Val  Ser  Glu  Asp  Leu  Asn  Gly  Thr  Val  Lys  Phe  Ser
               245                 250                      255

Ser  Ser  Leu  Pro  Tyr  Pro  Asn  Asn  Leu  Asn  Ser  Val  Leu  Ala  Glu  Arg
          260                 265                 270

Leu  Glu  Lys  Trp  Leu  Gln  Leu  Met  Leu  Met  Trp  His  Pro  Arg  Gln  Arg
          275                 280                 285
```

```
Gly  Thr  Asp  Pro  Thr  Tyr  Gly  Pro  Asn  Gly  Cys  Phe  Lys  Ala  Leu  Asp
     290                 295                 300

Asp  Ile  Leu  Asn  Leu  Lys  Leu  Val  His  Ile  Leu  Asn  Met  Val  Thr  Gly
305                      310                 315                           320

Thr  Ile  His  Thr  Tyr  Pro  Val  Thr  Glu  Asp  Glu  Ser  Leu  Gln  Ser  Leu
                    325                 330                           335

Lys  Ala  Arg  Ile  Gln  Gln  Asp  Thr  Gly  Ile  Pro  Glu  Glu  Asp  Gln  Glu
               340                      345                      350

Leu  Leu  Gln  Glu  Ala  Gly  Leu  Ala  Leu  Ile  Pro  Asp  Lys  Pro  Ala  Thr
          355                      360                      365

Gln  Cys  Ile  Ser  Asp  Gly  Lys  Leu  Asn  Glu  Gly  His  Thr  Leu  Asp  Met
     370                      375                 380

Asp  Leu  Val  Phe  Leu  Phe  Asp  Asn  Ser  Lys  Ile  Thr  Tyr  Glu  Thr  Gln
385                 390                      395                           400

Ile  Ser  Pro  Arg  Pro  Gln  Pro  Glu  Ser  Val  Ser  Cys  Ile  Leu  Gln  Glu
               405                      410                      415

Pro  Lys  Arg  Asn  Leu  Ala  Phe  Phe  Gln  Leu  Arg  Lys  Val  Trp  Gly  Gln
               420                 425                 430

Val  Trp  His  Ser  Ile  Gln  Thr  Leu  Lys  Glu  Asp  Cys  Asn  Arg  Leu  Gln
          435                      440                 445

Gln  Gly  Gln  Arg  Ala  Ala  Met  Met  Asn  Leu  Leu  Arg  Asn  Asn  Ser  Cys
     450                      455                 460

Leu  Ser  Lys  Met  Lys  Asn  Ser  Met  Ala  Ser  Met  Ser  Gln  Gln  Leu  Lys
465                      470                 475                           480

Ala  Lys  Leu  Asp  Phe  Phe  Lys  Thr  Ser  Ile  Gln  Ile  Asp  Leu  Glu  Lys
                    485                 490                      495

Tyr  Ser  Glu  Gln  Thr  Glu  Phe  Gly  Ile  Thr  Ser  Asp  Lys  Leu  Leu  Leu
               500                      505                 510

Ala  Trp  Arg  Glu  Met  Glu  Gln  Ala  Val  Glu  Leu  Cys  Gly  Arg  Glu  Asn
          515                      520                 525

Glu  Val  Lys  Leu  Leu  Val  Glu  Arg  Met  Met  Ala  Leu  Gln  Thr  Asp  Ile
     530                      535                 540

Val  Asp  Leu  Gln  Arg  Ser  Pro  Met  Gly  Arg  Lys  Gln  Gly  Gly  Thr  Leu
545                      550                 555                           560

Asp  Asp  Leu  Glu  Glu  Gln  Ala  Arg  Glu  Leu  Tyr  Arg  Arg  Leu  Arg  Glu
               565                      570                      575

Lys  Pro  Arg  Asp  Gln  Arg  Thr  Glu  Gly  Asp  Ser  Gln  Glu  Met  Val  Arg
               580                      585                      590

Leu  Leu  Leu  Gln  Ala  Ile  Gln  Ser  Phe  Glu  Lys  Lys  Val  Arg  Val  Ile
          595                      600                 605

Tyr  Thr  Gln  Leu  Ser  Lys  Thr  Val  Val  Cys  Lys  Gln  Lys  Ala  Leu  Glu
     610                      615                 620

Leu  Leu  Pro  Lys  Val  Glu  Glu  Val  Val  Ser  Leu  Met  Asn  Glu  Asp  Glu
625                      630                 635                           640

Lys  Thr  Val  Val  Arg  Leu  Gln  Glu  Lys  Arg  Gln  Lys  Glu  Leu  Trp  Asn
                    645                 650                      655

Leu  Leu  Lys  Ile  Ala  Cys  Ser  Lys  Val  Arg  Gly  Pro  Val  Ser  Gly  Ser
               660                      665                 670

Pro  Asp  Ser  Met  Asn  Ala  Ser  Arg  Leu  Ser  Gln  Pro  Gly  Gln  Leu  Met
          675                      680                 685

Ser  Gln  Pro  Ser  Thr  Ala  Ser  Asn  Ser  Leu  Pro  Glu  Pro  Ala  Lys  Lys
     690                      695                 700

Ser  Glu  Glu  Leu  Val  Ala  Glu  Ala  His  Asn  Leu  Cys  Thr  Leu  Leu  Glu
705                 710                      715                           720
```

| Asn | Ala | Ile | Gln | Asp | Thr | Val | Arg | Glu | Gln | Asp | Gln | Ser | Phe | Thr | Ala |
|-----|-----|-----|-----|-----|-----|-----|-----|-----|-----|-----|-----|-----|-----|-----|-----|
|     |     |     |     | 725 |     |     |     | 730 |     |     |     |     |     | 735 |     |
| Leu | Asp | Trp | Ser | Trp | Leu | Gln | Thr | Glu | Glu | Glu | Glu | His | Ser | Cys | Leu |
|     |     |     | 740 |     |     |     |     | 745 |     |     |     |     | 750 |     |     |
| Glu | Gln | Ala | Ser |     |     |     |     |     |     |     |     |     |     |     |     |
|     |     | 755 |     |     |     |     |     |     |     |     |     |     |     |     |     |

SCREENING METHOD FOR AGENTS THAT MODULATE HUMAN NIK ACTIVITY

This is a divisional application of U.S. Ser. No. 08/887,518, filed Jul. 3, 1997.

FIELD OF THE INVENTION

The field of this invention is proteins involved in transcription factor activation.

BACKGROUND

Cytokines trigger changes in gene expression by modifying the activity of otherwise latent transcription factors (Hill and Treisman, 1995). Nuclear factor κB (NF-κB) is a prominent example of how such an external stimulus is converted into an active transcription factor (Verma et al., 1995). The NF-κB system is composed of homo- and heterodimers of members of the Rel family of related transcription factors that control the expression of numerous immune and inflammatory response genes as well as important viral genes (Lenardo and Baltimore, 1989; Baeuerle and Henkel, 1994). The activity of NF-κB transcription factors is regulated by their subcellular localization (Verma et al., 1995). In most cell types, NF-κB is present as a heterodimer comprising of a 50 kDa and a 65 kDa subunit. This heterodimer is sequestered in the cytoplasm in association with IκBα a member of the IκB family of inhibitory proteins (Finco and Baldwin, 1995; Thanos and Maniatis, 1995; Verma et al., 1995). IκBα masks the nuclear localization signal of NF-κB and thereby prevents NF-κB nuclear translocation. Conversion of NF-κB into an active transcription factor that translocates into the nucleus and binds to cognate DNA sequences requires the phosphorylation and subsequent ubiquitin-dependent degradation of IκBα in the 26s proteasome. Signal-induced phosphorylation of IκBα occurs at serines 32 and 36. Mutation of one or both of these serines renders IκBα resistant to ubiquitination and proteolytic degradation (Chen et al., 1995); DiDonato, 1996 #370, Roff, 1996 #397.

The pleiotropic cytokines tumor necrosis factor (TNF) and interleukin-1 (IL-1) are among the physiological inducers of IκB phosphorylation and subsequent NF-κB activation (Osborn et al., 1989; Beg et al., 1993). Although TNF and IL-1 initiate signaling cascades leading to NF-κB activation via distinct families of cell-surface receptors (Smith et al., 1994; Dinarello, 1996), both pathways utilize members of the TNF receptor-associated factor (TRAF) family of adaptor proteins as signal transducers (Rothe et al., 1995; Hsu et al., 1996; Cao et al., 1996b). TRAF proteins were originally found to associate directly with the cytoplasmic domains of several members of the TNF receptor family including the 75 kDa TNF receptor (TNFR2), CD40, CD30, and the lymphotoxin-β receptor (Rothe et al., 1994; Hu et al., 1994; Cheng et al., 1995; Mosialos et al., 1995; Song and Donner, 1995; Sato et al., 1995; Lee et al., 1996; Gedrich et al., 1996; Ansieau et al., 1996). In addition, TRAF proteins are recruited indirectly to the 55 kDa TNF receptor (TNFR1) by the adaptor protein TRADD (Hsu et al., 1996). Activation of NF-κB by TNF requires TRAF2 (Rothe et al., 1995; Hsu et al., 1996). TRAF5 has also been implicated in NF-κB activation by members of the TNF receptor family (Nakano et al., 1996); Ishida, 1996 #240. In contrast, TRAF6 participates in NF-κB activation by IL-1 (Cao et al., 1996b). Upon IL-1 treatment, TRAF6 associates with IRAK, a serine-threonine kinase that binds to the IL-1 receptor complex (Cao et al., 1996a); Huang, 1997 #400.

An NF-κB-inducing kinase (NIK), a member of the MAP kinase kinase kinase (MAP3K) family, was identified as a TRAF2-interacting protein (Malinin et al., 1997). NIK activates NF-κB when overexpressed, and kinase-inactive mutants of NIK comprising its TRAF2-interacting C-terminal domain ($NIK_{(624-947)}$) or lacking two crucial lysine residues in its kinase domain ($NIK_{(KK429-430AA)}$) behave as dominant-negative inhibitors that suppress TNF-, IL-1-, and TRAF2-induced NF-κB activation (Malinin et al., 1997).

Here, we disclose a novel human NIK ($NIK_{(Ala25)}$), which also provides the foregoing functionalities yet deviates in terms of critical sequence and structural characteristics; in particular, a Pro-Ala substitution at position 25 imposes altered protein structure. We show that the $NIK_{(Ala25)}$ variant interacts with and cross-phosphorylates the IκB Kinases α and β, IKK-α and IKK-β (see Goeddel et al. and Rothe et al., copending applications T97-006 and T97-007, respectively, filed Jul. 1, 1997). IKK-α and IKK-β have sequence similarity to the conceptual translate of a previously identified open reading frame postulated to encode a serine-threonine kinase of unknown function ('Conserved Helix-loop-helix Ubiquitous Kinase' or CHUK, Connelly and Marcu, 1995; Mock et al., 1995). Catalytically inactive mutants of the IKKs suppress NF-κB activation induced by TNF and IL-1 stimulation as well as by TRAF and NIK overexpression; transiently expressed IKKs associate with the endogenous IκBα complex; and the IKKs phosphorylate IκBα on serines 32 and 36. As used herein, Ser32 and Ser36 of IκB refers collectively to the two serine residues which are part of the consensus sequence DSGL/IXSM/L (e.g. ser 32 and 36 in IκBα, ser 19 and 23 in IκBβ, and ser 157 and 161, or 18 and 22, depending on the usage of methionines, in IκBε, respectively. In addition, we disclose that $NIK_{(Ala25)}$ associates with other members of the TRAF family, including TRAF5 and TRAF6. Catalytically inactive mutants of $NIK_{(Ala25)}$ also inhibit TRAF5- and TRAF6-induced NF-κB activation, thus providing a unifying concept for $NIK_{(Ala25)}$ as a common mediator in the NF-κB signaling cascades triggered by TNF and IL-1 downstream of TRAFs.

SUMMARY OF THE INVENTION

The invention provides methods and compositions relating to isolated NIK polypeptides, related nucleic acids, polypeptide domains thereof having NIK-specific structure and activity and modulators of NIK function, particularly IKKβ/α kinase activity. NIK polypeptides can regulate NFκB activation and hence provide important regulators of cell function. The polypeptides may be produced recombinantly from transformed host cells from the subject NIK polypeptide encoding nucleic acids or purified from mammalian cells. The invention provides isolated NIK hybridization probes and primers capable of specifically hybridizing with the disclosed NIK gene, NIK-specific binding agents such as specific antibodies, and methods of making and using the subject compositions in diagnosis (e.g. genetic hybridization screens for NIK transcripts), therapy (e.g. NIK kinase inhibitors to inhibit TNF signal transduction) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

The nucleotide sequence of a natural human cDNA encoding a human NIK polypeptide is shown as SEQ ID NO:1, and the full conceptual translate is shown as SEQ ID NO:2. This novel NIK cDNA sequence was cloned by PCR using primers designed from GenBank accesion number Y102565. The NIK polypeptides of the invention include incomplete translates of SEQ ID NO:1 which translates and deletion mutants of SEQ ID NO:2 have human NIK-specific amino acid sequence, binding specificity or function and comprise Ala25. Preferred translates/deletion mutants comprise at least a 10 residue Ala25-containing domain of SEQ ID NO:2, preferably including residues 22–31, more preferably including residues 12–31, most preferably including residues 2–31. The subject domains provide NIK domain specific activity or function, such as NIK-specific kinase or kinase inhibitory activity, IKK-α/β (SEQ ID NO:3/4, respectively)-binding or binding inhibitory activity, TRAF1, 2, 3, 5 and/or 6 binding or binding inhibitory activity, IκB-binding or binding inhibitory activity, NFκB activating or inhibitory activity or antibody binding. Preferred domains phosphorylate at least one serine residue of IKK-α and/or β.

NIK-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an NIK polypeptide with a binding target is evaluated. The binding target may be a natural intracellular binding target such as an NIK substrate, a NIK regulating protein or other regulator that directly modulates NIK activity or its localization; or non-natural binding target such a specific immune protein such as an antibody, or an NIK specific agent such as those identified in screening assays such as described below. NIK-binding specificity may assayed by kinase activity or binding equilibrium constants (usually at least about $10^7 M^{-1}$, preferably at least about $10^8 M^{-1}$, more preferably at least about $10^9 M^{-1}$), by the ability of the subject polypeptide to function as negative mutants in NIK-expressing cells, to elicit NIK specific antibody in a heterologous host (e.g a rodent or rabbit), etc. In any event, the NIK binding specificity of the subject NIK polypeptides necessarily distinguishes that of the human NIK protein of Malinin et al. (1997).

The claimed NIK polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The NIK polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides binding agents specific to the claimed NIK polypeptides, including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g. NF-κB activation. Novel NIK-specific binding agents include NIK-specific receptors, such as somatically recombined polypeptide receptors like specific antibodies or T-cell antigen receptors (see, e.g. Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate NIK function, e.g. NIK-dependent transcriptional activation. For example, a wide variety of inhibitors of NIK IKK-α/β kinase activity may be used to regulate signal transduction involving IκB. Exemplary NIK kinase inhibitors include known classes of serine/threonine kinase (e.g. PKC) inhibitors such as competitive inhibitors of ATP and substrate binding, antibiotics, NIK-derived peptide inhibitors, esp. dominant negative deletion mutants, etc., see Tables 1 and 2. NIK specificity and activity are readily quantified in high throughput kinase assays using panels of protein kinases (see cited references and Examples).

Preferred inhibitors include natural compounds such as staurosporine (Omura S, et al. J Antibiot (Tokyo) 1995 Jul;48(7):535–48), produced by a marine organism, and synthetic compounds such as PD 153035, which also potently inhibits the EGF receptor protein kinase (Fry DW et al. Science 1994 Aug 19;265(5175):1093–5). Members of the tyrphostin family of synthetic protein kinase inhibitors are also useful; these include compounds which are pure ATP competitors, compounds which are pure substrate competitors, and compounds which are mixed competitors: compete with both ATP and substrate (Levitzki A and Gazit A, Science 1995 Mar 24;267(5205):1782–8). Additional NIK inhibitors include peptide-based substrate competitors endogenously made by the mammalian cell, e.g. PKI (protein kinase inhibitor, Seasholtz AF et al., Proc Natl Acad Sci USA 1995 Feb 28;92(5):1734–8), or proteins inhibiting cdc kinases (Correa-Bordes J and Nurse P, Cell 1995 Dec 15;83(6):1001–9). Additional small peptide based substrate competitive kinase inhibitors and allosteric inhibitors (inhibitory mechanisms independent of ATP or substrate competition) are readily generated by established methods (Hvalby O, et al. Proc Natl Acad Sci USA 1994 May 24;91(11):4761–5; Baja P, et al., Cell Immunol 1994 Jan;153 (1):28–38; Villar-Palasi C, Biochim Biophys Acta 1994 Dec 30;1224(3):384–8; Liu WZ, et al., Biochemistry 1994 Aug 23;33(33):10120–6).

TABLE I

Selected Small Molecule NIK Kinase Inhibitors

| Inhibitors | Citations |
| --- | --- |
| HA-100[1] | 1. Hagiwara, M,. et al. Mol. Pharmacol. 32: 7 (1987) |
| Chelerythrine[2] | 2. Herbert, J. M., et al. Biochem Biophys Res Com 172: 993 (1990) |
| Staurosporine[3,4,5] | 3. Schachtele, C., et al. Biochem Biophys Res Com 151: 542 (1988) |
| Calphostin C[6,7,8,9] | 4. Tamaoki, T., et al. Biochem Biophys Res Com 135: 397 (1986) |
| K-252b[10] | 5. Tischler, A. S., et al. J. Neurochemistry 55: 1159 (1990) |
| PKC 19–36[11] | 6. Bruns, R. F., et al. Biochem Biophys Res Com 176: 288 (1991) |
| Iso-H7[12] | 7. Kobayashi, E., et al. Biochem Biophys Res Com 159: 548 (1989) |
| PKC 19–31 | 8. Tamaoki, T., et al Adv2nd Mass Phosphoprotein Res 24: 497 (1990) |
| H-7[13,3,14] | 9. Tamaoki, T., et al. Biotechnology 8: 732 (1990) |
| H-89[15] | 10. Yasuzawa, T. J. Antibiotics 39: 1972 (1986) |
| KT5720[16] | 11. House, C., et al. Science 238: 1726 (1987) |
| cAMP-depPKinhib[17] | 12. Quick, J., et al. Biochem. Biophys. Res. Com. 167: 657 (1992) |
| A-3[18] | 13. Bouli, N. M. and Davis, M. Brain Res. 525: 198 (1990) |
| HA1004[19,20] | 14. Takahashi, I., et al. J. Pharmacol. Exp. Ther. 255: 1218 (1990) |
| K-252a[16,5] | 15. Chijiwa, T., et al. J. Biol. Chem. 265: 5267 (1990) |
| KT5823[16] | 16. Kase, H., et al. Biochem. Biophys. Res. Com. 142: 436 (1987) |
| ML-9[21] | 17. Cheng, H. C., et al. J. Biol. Chem. 261: 989 (1986) |
| KT5926[22] | 18. Inagaki, M., et al. Mol. Pharmacol. 29: 577 (1986) |
| | 19. Asano, T. and Hidaka, H. J Pharmaco. Exp Ther 231: 141 (1984) |
| | 20. Hidaka, H., et al. Biochemistry 23: 5036 (1984) |
| | 21. Nagatsu, T., et al. Biochem Biophys Res Com 143: 1045 (1987) |
| | 22. Nakanishi, S., et al. Mol. Pharmacol. 37: 482 (1990) |

TABLE II

Selected Peptidyl NIK Kinase Inhibitors

| | |
| --- | --- |
| hIKKα, residues 2–398 | NIK, residues 624–947 |
| hIKKα, residues 279–547 | NIK, residues 1–645, Ala429, Ala430 |
| hIκBβ, residues 5–381 | TRAF2, residues 225–501 |
| hIκBβ, residues 301–641 | TRAF6, residues 218–512 |

Accordingly, the invention provides methods for modulating signal transduction involving IκB in a cell comprising the step of modulating NIK kinase activity, e.g. by contacting the cell with a serine/threonine kinase inhibitor. The cell may reside in culture or in situ, i.e. within the natural host. Preferred inhibitors are orally active in mammalian hosts. For diagnostic uses, the inhibitors or other NIK binding agents are frequently labeled, such as with fluorescent, radioactive, chemiluminescent, or other easily detectable molecules, either conjugated directly to the binding agent or conjugated to a probe specific for the binding agent.

The amino acid sequences of the disclosed NIK polypeptides are used to back-translate NIK polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural NIK-encoding nucleic acid sequences ("GCG" software, Genetics Computer Group, Inc, Madison Wis.). NIK-encoding nucleic acids used in NIK-expression vectors and incorporated into recombinant host cells, e.g. for expression and screening, transgenic animals, e.g. for functional studies such as the efficacy of candidate drugs for disease associated with NIK-modulated cell function, etc.

The invention also provides nucleic acid hybridization probes and replication/amplification primers having a NIK cDNA specific sequence comprising SEQ ID NO:1, bases 72–75, and sufficient to effect specific hybridization thereto (i.e. specifically hybridize with SEQ ID NO:1 in the presence of the NIK cDNA described by Malinin et al. (1997). Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18M NaCl, 0.01M NaPO$_4$, pH7.7, 0.001M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. NIK nucleic acids can also be distinguished using alignment algorithms, such as BLASTX (Altschul et al. (1990) Basic Local Alignment Search Tool, J Mol Biol 215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO:1, or fragments thereof comprising SEQ ID NO:1, bases 72–75, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of NIK genes and gene transcripts and in detecting or amplifying nucleic acids encoding additional NIK homologs and structural analogs. In diagnosis, NIK hybridization probes find use in identifying wild-type and mutant NIK alleles in clinical and laboratory samples. Mutant alleles are used to generate allele-specific oligonucleotide (ASO) probes for high-throughput clinical diagnoses. In therapy, therapeutic NIK nucleic acids are used to modulate cellular expression or intracellular concentration or availability of active NIK.

The invention provides efficient methods of identifying agents, compounds or lead compounds for agents active at the level of a NIK modulatable cellular function. Generally, these screening methods involve assaying for compounds which modulate NIK interaction with a natural NIK binding target such as IKKα and/or β, TRAF1, 2, 3, 5 or 6, etc. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an NIK polypeptide, which may be part of a fusion product with another peptide or polypeptide, e.g. a tag for detection or anchoring, etc. The assay mixtures comprise a natural intracellular NIK binding target. In a particular embodiment, the binding target is a a IKKα and/or β-derived substrate of NIK kinase activity. Such substrates comprise a NIK-phosphoylatable IKKα and/or β serine residue and at least 5, preferably at least 10, and more preferably at least 20 naturally occurring immediately flanking residues on each side. While native full-length binding targets may be used, it is frequently preferred to use portions (e.g. peptides) thereof so long as the portion provides binding affinity and avidity to the subject NIK polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like ATP or ATP analogs (for kinase assays), salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the NIK polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the NIK polypeptide and one or more binding targets is detected by any convenient way. For NIK kinase assays, 'binding' is generally detected by a change in the phosphorylation of a NIK substrate. In this embodiment, kinase activity may quantified by the transfer to the substrate of a labeled phosphate, where the label may provide for direct detection as radioactivity, luminescence, optical or electron density, etc. or indirect detection such as an epitope tag, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the NIK polypeptide to the target in the absence of the agent as compared with the binding affinity in the presence of the agent indicates that the agent modulates the binding of the NIK polypeptide to the NIK binding target. Analogously, in the cell-based assay also described below, a difference in NIK-dependent transcriptional activation in the presence and absence of an agent indicates the agent modulates NIK function. A difference, as used herein, is statistically significant and preferably represents at least a 50%, more preferably at least a 90% difference.

Parenthetical References

Ansieau, S., et al. (1996). Proc. Natl. Acad. Sci. USA 93, 14053–14058.

Baeuerle, P. A., and Henkel, T. (1994). Annu. Rev. Immunol. 12, 141–179.

Beg, A. A., et al. (1993). Mol. Cell. Biol. 13, 3301–3310.

Cao, Z., Henzel, W. J., and Gao, X. (1996a). Science 271, 1128–1131.

Cao, Z., et al. (1996b). Nature 383, 443–446.

Chen, Z., et al.. (1995). Genes Dev. 9, 1586–1597.

Cheng, G., et al. (1995). Science 267, 1494–1498.

Connelly, M. A., and Marcu, K. B. (1995). Cell. Mol. Biol. Res. 41, 537–549.

Dinarello, C. A. (1996) Blood 87, 2095–2147.

Fields, S., and Song, O. -k. (1989). Nature 340, 245–246.

Finco, T. S., and Baldwin, A. S. (1995). Immunity 3, 263–272.

Gedrich, R. W., et al. (1996). J. Biol. Chem. 271, 12852–12858.

Hill, C. S., and Treisman, R. (1995). Cell 80, 199–211.

Hsu, H., Shu, H. -B., Pan, M. -P., and Goeddel, D. V. (1996). Cell 84, 299–308.

Hu, H. M., et al. (1994). J. Biol. Chem. 269, 30069–30072.

Lee, S. Y., et al. (1996). Proc. Natl. Acad. Sci. USA 93, 9699–9703.

Lenardo, M., and Baltimore, D. (1989). Cell 58, 227–229.

Malinin, N. L., et al. (1997). Nature 385, 540–544.

Mock et al. (1995). Genomics 27, 348–351.

Mosialos, G., et al. (1995). Cell 80, 389–399.

Nakano, H., et al. (1996). J. Biol. Chem. 271, 14661–14664.

Osborn, L., Kunkel, S., and Nabel, G. J. (1989) Proc Natl Aca Sci USA 86, 2336–2340.

Rothe, M., Sarma, V., Dixit, V. M., and Goeddel, D. V. (1995) Science 269, 1424–1427.

Rothe, M., Wong, S. C., Henzel, W. J., and Goeddel, D. V. (1994). Cell 78, 681–692.

Sato, T., Irie, S., and Reed, J. C. (1995). FEBS Lett. 358, 113–118.

Schindler, U., and Baichwal, V. R. (1994). Mol. Cell. Biol. 14, 5820–5831.

Smith, C. A., Farrah, T., and Goodwin, R. G. (1994). Cell 76, 959–962.

Song, H. Y., and Donner, D. B. (1995). Biochem. J. 809, 825–829.

Thanos, D., and Maniatis, T. (1995). Cell 80, 529–532.

Verma, I. M., et al. (1995). Genes Dev. 9, 2723–2735.

The following experimental section and examples are offered by way of illustration and not by way of limitation.

EXAMPLES

1. Protocol for at NIK-IKK-β Phosphorylation Assay

A. Reagents

Neutralite Avidin: 20 μg/ml in PBS.

kinase: $10^{-8}$–$10^{-5}$M NIK kinase domain deletion mutant (SEQ ID NO:2, residues 2–644) at 20 μg/ml in PBS.

substrate: $10^{-7}$–$10^{-4}$M biotinylated IKK-β (SEQ ID NO:4) substrate at 40 μg/ml in PBS.

Blocking buffer: 5% BSA, 0.5% Tween 20 in PBS; 1 hour at room temperature.

Assay Buffer: 100 mM KCl, 10 mM $MgCl_2$, 1 mM $MnCl_2$, 20 mM HEPES pH 7.4, 0.25 mM EDTA, 1% glycerol, 0.5% NP-40, 50 mM BME, 1 mg/ml BSA, cocktail of protease inhibitors.

[$^{32}$P]γ-ATP 10× stock: $2×10^{-5}$M cold ATP with 100 μCi [$^{32}$P]γ-ATP. Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVo_3$ (Sigma # S-6508) in 10 ml of PBS.

B. Preparation of Assay Plates

Coat with 120 μl of stock N Avidin per well overnight at 4° C.

Wash 2 times with 200 μl PBS.

Block with 150 μl of blocking buffer.

Wash 2 times with 200 μl PBS.

C. Assay

Add 40 μl assay buffer/well.

Add 40 μl biotinylated substrate (2–200 pmoles/40 ul in assay buffer)

Add 40 μl kinase (0.1–10 pmoles/40 ul in assay buffer)

Add 10 μl compound or extract.

Add 10 μl [$^{32}$P]γ-ATP 10× stock.

Shake at 25° C. for 15 minutes.

Incubate additional 45 minutes at 25° C.

Stop the reaction by washing 4 times with 200 μl PBS.

Add 150 μl scintillation cocktail.

Count in Topcount.

D. Controls For All Assays (Located On Each Plate)

a. Non-specific binding b. cold ATP at 80% inhibition.

2. Protocol For High Throughput NIKI-TRAF2 Binding Assay

A. Reagents

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P NIK polypeptide 10× stock: $10^{-8}$–$10^{-6}$M "cold" NIK supplemented with 200,000–250,000 cpm of labeled NIK (Beckman counter). Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVO_3$ (Sigma # S-6508) in 10 ml of PBS.

TRAF2: $10^{-7}$–$10^{-5}$M biotinylated TRAF2 in PBS.

B. Preparation of Assay Plates

Coat with 120 μl of stock N-Avidin per well overnight at 4° C.

Wash 2 times with 200 μl PBS.

Block with 150 μl of blocking buffer.

Wash 2 times with 200 μl PBS.

C. Assay

Add 40 μl assay buffer/well.

Add 10 μl compound or extract.

Add 10 μl $^{33}$P-NIK (20–25,000 cpm/0.1–10 pmoles/well= $10^{-9}$–$10^{-7}$M final conc).

Shake at 25° C. for 15 minutes.

Incubate additional 45 minutes at 25° C.

Add 40 μM biotinylated TRAF2 (0.1–10 pmoles/40 ul in assay buffer)

Incubate 1 hour at room temperature.

Stop the reaction by washing 4 times with 200 μM PBS.

Add 150 μM scintillation cocktail.

Count in Topcount.

D. Controls For All Assays (Located On Each Plate)

a. Non-specific binding b. Soluble (non-biotinylated TRAF2) at 80% inhibition.

3. Protocol For High Throughput IκB-complex Formation Assay

A. Reagents

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P NIK polypeptide 10× stock: $10^{-8}$–$10^{-6}$M "cold" NIK supplemented with 200,000–250,000 cpm of labeled NIK (Beckman counter). Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVO_3$ (Sigma # S-6508) in 10 ml of PBS.

IκB: $10^{-7}$–$10^{-5}$M biotinylated IκB in PBS.

IKK-β: $10^{-7}$–$10^{-5}$M in PBS.

B. Preparation of Assay Plates

Coat with 120 μl of stock N-Avidin per well overnight at 4° C.

Wash 2 times with 200 μl PBS.

Block with 150 μl of blocking buffer.

Wash 2 times with 200 μl PBS.

C. Assay

Add 40 μl assay buffer/well.

Add 10 μl compound or extract.

Add 10 μl $^{33}$P-NIK (20–25,000 cpm/0.1–10 pmoles/well= $10^{-9}$–$10^{-7}$M final conc).

11

Shake at 25° C. for 15 minutes.
Incubate additional 45 minutes at 25° C.
Add 20 μM IKK-β (0.1–10 pmoles/20 ul in assay buffer)
Add 20 μM biotinylated IκB (0.1–10 pmoles/20 ul in assay buffer)
Incubate 1 hour at room temperature.
Stop the reaction by washing 4 times with 200 μM PBS.
Add 150 μM scintillation cocktail.
Count in Topcount.
D. Controls For All Assays (Located On Each Plate)
   a. Non-specific binding

12 b. Soluble (non-biotinylated IκB) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of screening for an agent which modulates the interaction of a nuclear factor-κB-inducing kinase (NIK) polypeptide with a NIK binding target, said method comprising the steps of:

incubating a mixture comprising:

an isolated polypeptide comprising at least 10 consecutive amino acid residues of the amino acid sequence set forth as SEQ ID NO:2, which consecutive amino acid residues comprise the amino acid residue 25 of SEQ ID NO:2, a binding target of said isolated polypeptide, and a candidate agent, under conditions whereby, but for the presence of said candidate agent, said isolated polypeptide specifically binds said binding target of said isolated polypeptide at a reference affinity and detecting the binding affinity of said isolated polypeptide to said binding target of said isolated polypeptide to determine an agent-biased affinity, wherein a difference between the agent-biased affinity and the reference affinity indicates that said candidate agent is an agent that modulates the interaction of said NIK polypeptide with said NIK binding target.

2. The method according to claim 1, wherein said isolated polypeptide has one or more activities selected from the group consisting of: kinase activity, kinase inhibitory activity, IκB kinase-α binding activity, IκB kinase-α binding inhibitory activity, IκB kinase-β binding activity, IκB kinase-β binding inhibitory activity, tumor necrosis factor receptor-associated factor 2 binding activity, tumor necrosis factor receptor-associated factor 2 binding inhibitory activity, IκB binding activity, IκB binding inhibitory activity, nuclear factor-κB activating activity and nuclear factor-κB inhibitory activity.

3. The method according to claim 1, wherein said isolated polypeptide comprises the amino acid sequence set forth as amino acid residues 22–31 of SEQ ID NO:2.

4. The method according to claim 1, wherein said isolated polypeptide comprises the amino acid sequence set forth as amino acid residues 12–31 of SEQ ID NO:2.

5. The method according to claim 1, wherein said isolated polypeptide comprises the amino acid sequence set forth as amino acid residues 2–31 of SEQ ID NO:2.

6. The method according to claim 1, wherein said isolated polypeptide comprises the amino acid sequence set forth as SEQ ID NO:2.

7. The method according to claim 1, wherein said binding target of said isolated polypeptide is a natural intracellular substrate and said reference affinity and said agent-biased affinity are detected as phosphorylation of said substrate.

8. The method according to claim 7 wherein said substrate comprises an IκB kinase (IKK) polypeptide domain.

9. The method according to claim 7 wherein said substrate comprises an IKK polypeptide domain and said isolated polypeptide comprises the amino acid sequence set forth as SEQ ID NO:2.

\* \* \* \* \*